United States Patent [19]

Poettgen

[11] Patent Number: 4,945,924
[45] Date of Patent: * Aug. 7, 1990

[54] STERILIZABLE REFLECTIVE SURGICAL DRAPE

[75] Inventor: Robert J. Poettgen, Arlington, Tex.

[73] Assignee: O.R. Concepts, Inc., Roanoke, Tex.

[*] Notice: The portion of the term of this patent subsequent to Aug. 23, 2005 has been disclaimed.

[21] Appl. No.: 234,314

[22] Filed: Aug. 19, 1988

Related U.S. Application Data

[63] Continuation-in-part of Ser. No. 890,402, Jul. 25, 1986, Pat. No. 4,765,323.

[51] Int. Cl.$^5$ .................. B32B 15/00; B32B 17/00
[52] U.S. Cl. ........................... 128/849; 5/502
[58] Field of Search .............. 128/849, 854, 862, 156; 2/69.5, 69, DIG. 7; 161/218; 156/254, 244.27; 5/502, 483, 483, 484, 500; 428/286, 425, 461

[56] References Cited

U.S. PATENT DOCUMENTS

| | | | |
|---|---|---|---|
| 2,897,109 | 7/1959 | Voigtman | 156/244.27 |
| 3,538,912 | 11/1970 | Becker | 128/155 |
| 3,539,374 | 11/1970 | Isaacson | 428/461 |
| 3,561,440 | 2/1971 | Bayer | 128/132 D |
| 3,565,067 | 2/1971 | Bayer | 128/132 D |
| 3,589,975 | 6/1971 | Andrews | 428/458 |
| 3,665,918 | 5/1972 | Lindquist | 128/156 |
| 3,667,458 | 6/1972 | Krebs | 128/132 D |
| 3,718,528 | 2/1973 | Bergstrom | 161/218 |
| 3,809,077 | 5/1974 | Hansen | 128/132 D |
| 3,813,315 | 5/1974 | Valyi | 156/254 |
| 3,934,582 | 1/1976 | Gorrie | 128/856 |
| 4,018,646 | 4/1977 | Ruffo | 428/425 |
| 4,334,529 | 6/1982 | Wirth | 128/132 D |
| 4,414,968 | 11/1983 | Amin | 128/853 |
| 4,433,019 | 2/1984 | Chumbley | 428/286 |
| 4,433,026 | 2/1984 | Molde | 428/252 |
| 4,471,769 | 9/1984 | Lockhart | 128/849 |
| 4,476,593 | 10/1984 | Fanselow et al. | 5/417 |
| 4,479,492 | 10/1984 | Singer | 128/132 D |
| 4,508,776 | 4/1985 | Smith | 2/69.5 |
| 4,524,767 | 6/1985 | Glassman | 128/854 |
| 4,637,947 | 1/1987 | Maekawa et al. | 428/68 |
| 4,715,366 | 12/1987 | Teeple | 128/852 |
| 4,765,323 | 8/1988 | Poettgen | 5/502 |

FOREIGN PATENT DOCUMENTS

WO85/03216 8/1985 European Pat. Off.
1263071 2/1972 United Kingdom.

OTHER PUBLICATIONS

Dyde et al., Thorax, 25: 355 (1970).
Radford et al., Br. J. Anaesth., 51: 237 (1979).
Bourke et al., Anesthesiology, 60: 151 (1984).
Cundy, Br. J. Anaesth., 52: 359 (1980).

*Primary Examiner*—Robert A. Hafer
*Assistant Examiner*—Michael A. Brown
*Attorney, Agent, or Firm*—Haynes and Boone

[57] ABSTRACT

A sterilizable, lightweight reflective surgical drape which is effective in reducing the rate of heat loss in human patients and may be used to provide a sterile surgical environment and an effective barrier to bacterial migration throughout a surgical procedure. The drape has non-conductive metallized plastic sheeting and at least one of a layer of thermoplastic material and a layer of flexible non-woven sterilizable material.

In a preferred embodiment, the drape of the present invention has a non-conductive first layer of aluminum and a second layer of a thermoplastic material. An optional third layer of a thermoplastic material is attached to the non-conductive first layer of aluminum.

In another preferred embodiment, the drape of the present invention has a non-conductive first layer of aluminum and a second layer of flexible non-woven sterilizable material. An optional third layer of flexible non-woven sterilizable material is attached to the non-conductive first layer of aluminum.

27 Claims, 2 Drawing Sheets

STERILIZABLE REFLECTIVE SURGICAL DRAPE

This application is a continuation-in-part of application Ser. No. 890,402 filed July 25, 1986 now U.S. Pat. No. 4,765,323 issued Aug. 23, 1988.

BACKGROUND OF THE INVENTION

1. Field of the Invention

The present invention relates to a sterilizable, lightweight reflective surgical drape which is effective in reducing the rate of heat loss in human patients and may be used to provide a sterile barrier for doctors and patients during a variety of surgical procedures.

2. Description of the Prior Art

Heat loss in human Patients during surgical procedures often leads to intraoperative hypothermia. Such hypothermia is caused in Part by anesthesia which depresses the thermal regulating centers in the hypothalamus. Also, general anesthetics and muscle relaxants block the shivering response and reduce metabolic heat Production. Moreover, the use of cold, dry anesthetic gases increases evaporative heat losses in the lungs, and peripheral vasodilatation makes the patient nearly poikilothermic. In a cool operating room, reduction of a patient's body temperature to 32° to 34° C. (89.6° to 93.2° F.) is not uncommon if preventive measures are not taken. Intraoperative hypothermia is responsible for a reduction in the rate of drug metabolism, an alteration in cerebral and regional blood flow, variations in EEG recordings and increased latency to post-surgical arousal.

In general, body temperature is determined by the balance between heat production and heat loss. Euthermia is maintained by the body's ability to vary heat production and to conserve heat. An anesthetized patient, with a relatively low metabolic rate and minimal control over heat loss, is obviously at a disadvantage. Metabolic heat production in an anesthetized normal adult male is 60–70 kcal per hour. Heat is lost through four parallel pathways: conduction, evaporation, convection, and radiation. Of these, conduction and evaporation cause the fewest intraoperative problems. Conductive loss is minimal (less than 10%) because of the low specific heat and conductivity of conventional drapes and mattresses. Although evaporative heat loss (i.e., insensible perspiration plus evaporation from the respiratory tract) is approximately 25 kcal per hour, this loss can be reduced to $10 \propto 15$ kcal per hour by using moist warm-inspired gases.

The major causes of heat loss in the operating room are convection and radiation. Convective heat loss is a function of ambient temperature and the square root of air velocity. In a 21° C. operating room, an exposed patient's convective heat loss can be as high as 80 kcal per hour. Conventional surgical draping reduces both the velocity and volume of air interacting with a patient's body and accordingly decreases convective heat loss to about 20 kcal per hour.

The human body is nearly a perfect emitter and absorber at the wavelengths involved in thermal exchange. Since the probability of photon reflection is nearly zero in a typical operating room, radiant heat loss is a function of the difference between the patient's body temperature and the temperature of the operating room. In a 21° C. operating room, a patient's radiant heat loss can be as high as 100 kcal per hour. Accordingly, it is the rate and degree of a patient's radiant heat loss that must be reduced to prevent the onset of intraoperative hypothermia.

Changes in body temperature that lead to intraoperative hypothermia occur more frequently in pediatric patients and carry greater risks than those in adults. A sick infant is unable to maintain thermal stability and dehydration, diarrhea and weakness serve to increase heat loss. Infants on the operating table may lose considerable amounts of heat both by convection into the air-conditioned operating room and by radiation to the cool walls. The resultant low body temperature is one of the most common causes of the stoppage of breathing following general anesthesia. Frequently the infant must be rewarmed before spontaneous respiration resumes. It is therefore essential that an infant in the operating room be kept normothermic.

Unsuspected hypothermia also particularly affects the elderly, whose ability to increase heat production and to decrease heat loss by vasoconstriction in response to cold is impaired. Hypothermia in the elderly is particularly troublesome since it leads to post-anesthetic shivering (PAS). Many complications arise from PAS due to the markedly increased demand on the cardiovascular and pulmonary systems. With age, cardiovascular and pulmonary physiology decline, resulting in less reserve capacity and borderline compensated function. Therefore, particularly in older patients with generally compromised physical condition, additional care must be taken to avoid intraoperative hypothermia and the resultant PAS.

It is therefore apparent that a need exists for a viable method and apparatus for preventing heat loss in all surgical patients. Many different methods and apparatus including pre-warmed gel-filled mattresses, blankets with circulating warm liquid, suits with circulating warm liquid, heating lamps, radiant heaters, humidification of inspired gases and conductive metallized plastic sheeting have been utilized in an attempt to minimize heat loss in patients during surgery.

Heat loss in infants has been conventionally minimized by keeping the infant in an incubator until the last moment, by wrapping all extremities in cotton cast padding, and by exposing as little of the body as possible during induction of anesthesia. The use of warmed, humidified anesthetic gases has also been used in preventing heat loss in infants. Heat has also been supplied by placing a warming mattress just beneath the operating table cover, by increasing the operating room temperature to 24° to 27° C. (75° to 80° F.) or by performing the operation beneath a radiant heater especially when operating on premature infants.

The active methods of warming mentioned above carry the risks of overheating or burning the patient while humidification of inspired gases increases the risk of bacterial or viral contamination in the breathing circuit. The use of conductive metallized plastic sheeting is discussed below. As noted above, another conventional method of preventing heat loss in surgical patients has been to raise the ambient temperature in the operating room to 24° to 27° C. Surgeons, however, are most comfortable when the operating room temperature is 18° C. while anesthesiologists prefer a temperature of 22° C. Accordingly, this technique of preventing heat loss in surgical patients has obvious drawbacks.

The use of conductive metallized plastic sheeting to reduce radiant heat loss was reported by Dyde and Lunn in 1970 (Thorax (1970), 25, 355). Dyde and Lunn proposed wrapping the lower half of a patient's body in a blanket of aluminum foil coated with polyethylene in an attempt to reduce heat loss during thoracotomy. Dyde and Lunn had good success in reducing heat loss in patients undergoing relatively short thoracotomy procedures.

Radford and Thurlow (*Br. J. Anesth.* (1979), 51, 237) later found that the type of metallized plastic sheeting used by Dyde and Lunn was ineffective in the Prevention of hypothermia in adult patients studied during neurosurgical operations. They concluded that active warming systems were needed to maintain normothermia in patients undergoing neurosurgical operations.

Radford and Thurlow used a type of metallized plastic sheeting made by Thermos under the name of "Space Blanket". Each blanket consisted of two layers of metallized plastic sheeting separated by an artificial fiber layer. Each patient in the control group wore a cotton gown and was covered by one cotton blanket. Each patient in the study group was additionally wrapped in metallized plastic sheeting. The head and shoulders were left exposed, as was the distal part of any limb with an arterial or venous cannula in place. No active warming system was used.

Radford and Thurlow theorized that a drawback of metallized plastic sheeting is that the infrared reflecting property of the metallic surface is reduced or lost by condensed perspiration. This theory may explain the inconsistencies in the results reported by Dyde and Lunn, and those reported by Radford and Thurlow.

Shortly after the publication of the Radford and Thurlow article one commentator observed that the insulation layer in metallized plastic sheeting is thin and that a breakdown may occur. *Brit. J. Anesthesia* (1980), 52, 359. The commentator concluded that, if metallized plastic sheeting is used in conjunction with electro-cautery there is a serious risk of burns from aberrant earthing. Thus, the prevailing view was that there was a significant electrical hazard present when space blankets or metallized plastic sheeting was used with electro-cautery units and metal operating tables.

Bourke, D. L. et al. (Intraoperative Heat Conservation Using a Reflective Blanket, *Anesthesiolgy*, 60: 151–154, 1984) studied the effectiveness of a reflective blanket in reducing radiant heat loss in an anesthetized patient. The reflective blanket used in the Bourke study was aluminized Tyvek, type 1443, which is used as a lining in survival apparel. All patients in the Bourke study were placed on an active heating blanket whose temperature had equilibrated with ambient temperature. The test patients were wrapped in the aluminized blanket as completely as positioning would allow. The blanket utilized in this study was perforated so that it would not trap moisture that could condense and cause skin maceration during prolonged use. The blanket utilized in this study was apparently conductive since a copper cable was used to connect the aluminized blanket to the operating table to prevent patient isolation. Also, as noted above, an aluminized blanket having a thin layer that may easily break down so that the blanket becomes perforated Poses a significant electrical hazard in the operating room environment. Thus, the reflective blanket utilized in the Bourke study would appear to pose a significant electrical hazard in the operating room environment.

In all surgical procedures, a patient is draped and/or otherwise covered with a sterile covering to prevent the prepared area of surgical interest from becoming contaminated by contact with unprepared areas or surfaces. Conventional sterile draping and covering materials, however, do not aid in the reduction of a patient's heat loss during a surgical procedure.

It is therefore apparent that there is a need for an apparatus that not only provides a sterile surgical environment and an effective barrier to bacterial migration throughout a surgical procedure, but also reduces intraoperative heat loss.

SUMMARY OF THE INVENTION

The sterilizable reflective surgical drape of the present invention avoids the above-mentioned disadvantages which are characteristic of the prior art. The sterilizable reflective surgical drape of the present invention is non-conductive and puncture resistant and therefore does not pose an electrical hazard in the operating room environment.

The sterilizable reflective surgical drape of the present invention has utility in reducing a patient's rate of heat loss during a surgical procedure. The drape of the present invention also enhances intraoperative EEG monitoring in neurosurgical patients. The drape also has potential application in neonatal and adult intensive care facilities. The drape is quite versatile in the resPect that it may be used for a variety of surgical procedures and may take several forms, including full and partial body length drapes, as well as leggings and caps.

In a first embodiment, the sterilizable reflective surgical drape of the present invention comprises non-conductive metallized plastic sheeting and at least one of (a) a layer of thermoplastic material; and, (b) a layer of flexible non-woven sterilizable material.

In a specific embodiment thereof, the sterilizable reflective surgical drape of the present invention comprises a non-conductive core layer of aluminum and a first and second adjacent layer of a thermoplastic material. A layer of flexible non-woven sterilizable material is attached to either the first or second adjacent layer of thermoplastic material.

In further specific embodiments thereof, the sterilizable reflective surgical drape of the present invention comprises a non-conductive first layer of aluminum and a second layer of thermoplastic material. A third layer of flexible non-woven sterilizable material is attached to either the non-conductive first layer of aluminum or the second layer of thermoplastic material.

In a still further specific embodiment thereof, the drape of the present invention comprises a non-conductive core layer of aluminum and a first and second adjacent layer of thermoplastic material.

In a second embodiment, the sterilizable reflective surgical drape of the present invention comprises non-conductive metallized plastic sheeting.

In a third embodiment, the sterilizable reflective surgical drape of the present invention comprises a non-conductive first layer of aluminum and a second adjacent layer of flexible non-woven sterilizable material. Optionally, a third adjacent layer of flexible non-woven sterilizable material is attached to the first layer of aluminum.

BRIEF DESCRIPTION OF THE DRAWINGS

In describing the invention, reference will be made to the accompanying drawings in which.

DETAILED DESCRIPTION OF THE PREFERRED EMBODIMENTS

Figure 1:
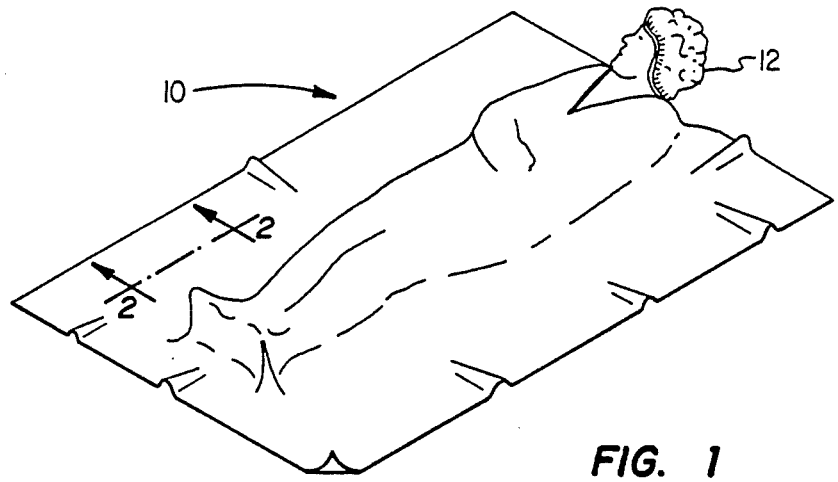
FIG. 1 is a perspective view of the sterilizable reflective surgical drape of the present invention.

Referring now to the drawings, and in particular FIG. 1, a sterilizable reflective surgical drape generally indicated at 10 is used for covering a surgical patient and reducing heat loss from the patient's body during a surgical procedure. In addition to preventing heat loss, when the drape 10 is sterilized by conventional procedures well-known to those skilled in the art, it may be used as a sterile drape.

Figure 3:
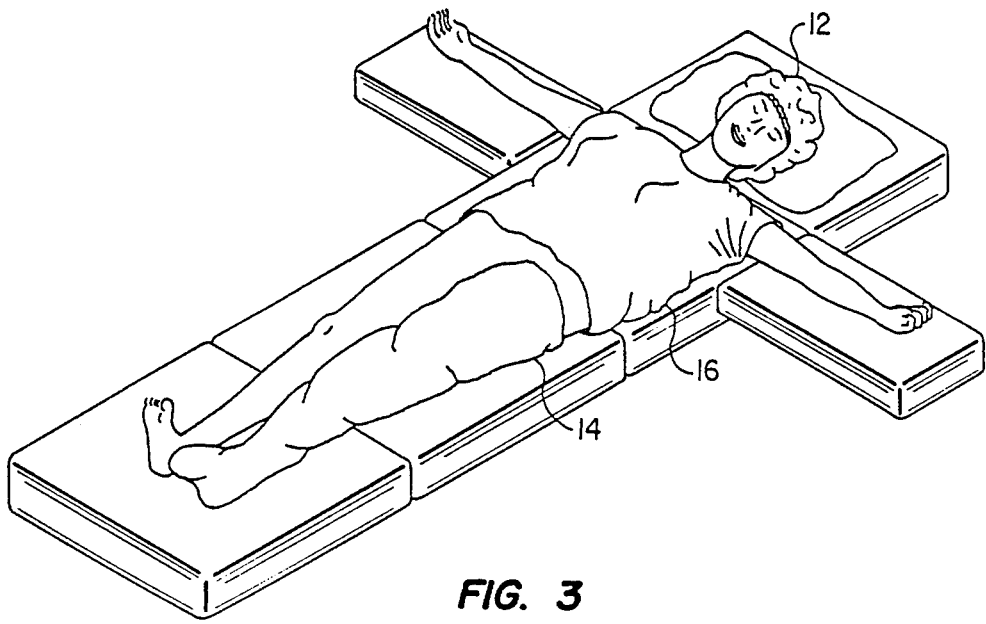
FIG. 3 is a perspective view showing various forms of the sterilizable reflective surgical drape of the present invention covering the left leg, torso and head of a human patient.

As shown in FIG. 1, the sterilizable reflective surgical drape 10 may be fashioned as a blanket which may be wrapped closely about a portion or the entire body of a patient undergoing a surgical procedure. As shown in FIGS. 1 and 3 the sterilizable reflective surgical drape may be fashioned as a cap 12 which serves as a head covering for a surgical patient. Those skilled in the art will recognize that the cap may be provided with a peripheral elastic band or other means to ensure the cap remains on the patient's head. Also as shown in FIG. 3, the sterilizable reflective surgical drape may be fashioned as leggings 14 which comprise an open end for receiving a patient s leg and an opposite closed end. Additionally, as shown in FIG. 3 the sterilizable reflective surgical drape may be fashioned as a covering 16 for the torso of a patient undergoing a surgical procedure. Those skilled in the art will recognize that the sterilizable reflective surgical drape may be fashioned in any desired conformation to cover any selected portion of the body of a patient undergoing a surgical procedure.

Figure 4:
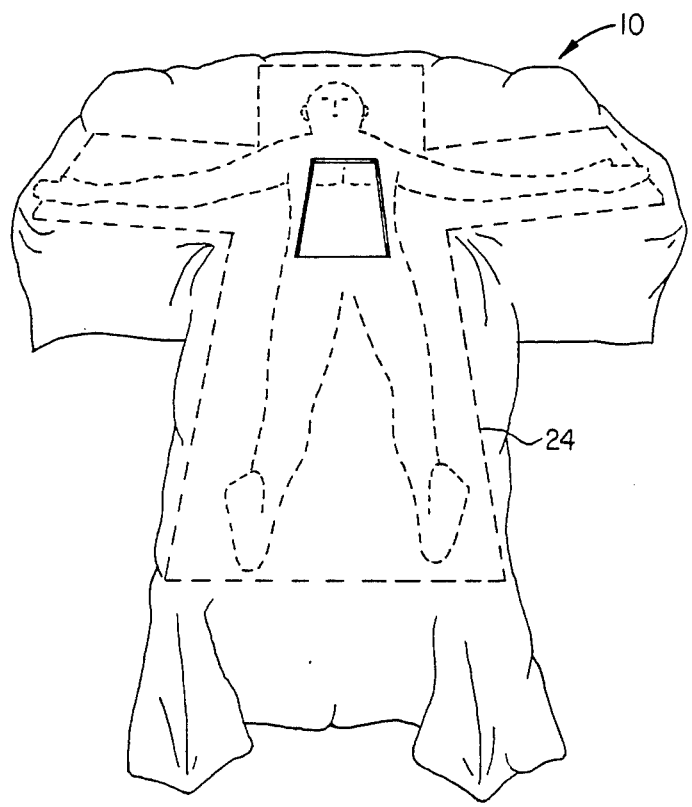
FIG. 4 is a perspective view of the sterilizable reflective surgical drape of the present invention covering the body of a human patient as a sterile drape.

As noted above, when sterilized by conventional procedures, the sterilizable reflective surgical drape of the present invention may be used as a sterile drape. As shown in FIG. 4, when used as a sterile drape 10, it is preferred that, the metallized portion 24 of the drape 10 extends only so far as necessary to cover the patient's body. Those skilled in the art will recognize that suitable and conventional fenestrations can be provided in the sterilizable reflective surgical drape to provide access through the drape to a desired portion of the body of a patient undergoing a surgical procedure.

Figure 2:
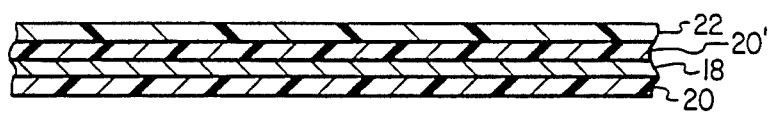
FIG. 2 is a section taken along line 2—2 of FIG. 1.

As shown in FIG. 2, one embodiment of the drape 10 of the present invention is a four-layer drape having a core layer 18, first and second adjacent layers 20,20', and an outer layer 22 attached to the second adjacent layer 20'. Those skilled in the art will recognize that outer layer 22 may be attached to either the first or second adjacent layers 20,20'. The core layer 18 comprises aluminum and is non-conductive. The first and second adjacent layers 20, 20' comprise a thermoplastic material. The outer layer 22 comprises a flexible non-woven sterilizable material.

The non-conductive core layer 18 of aluminum, preferably, is vacuum deposited or sputtered in a non-continuous manner on the first adjacent layer 20 of thermoplastic material. Those skilled in the art will recognize that the aluminum can be replaced by other heat reflective metals such as gold and silver. In a preferred embodiment, the layer of aluminum has a thickness of from 270 Å to 330 Å, and in a most preferred embodiment, it has a thickness of approximately 300 Å. The non-conductive core layer 18 of aluminum is preferably substantially enclosed or sandwiched between the first and second adjacent layers 20,20' of thermoplastic material. The second adjacent layer 20' of thermoplastic material is preferably laminated to the non-conductive core layer 18 of aluminum using an adhesive. The adhesive is preferably moisture-proof and is most preferably an acrylic moisture-proof adhesive. Alternatively, the second adjacent layer 20' of thermoplastic material is preferably heat extruded to the non-conductive core layer 18 of aluminum. Those skilled in the art will recognize that other suitable methods may be utilized for permanently adhering the second adjacent layer 20 of thermoplastic material to the non-conductive core layer 18 of aluminum.

The thermoplastic material of the first and second adjacent layers 20,20' must be flexible but need not be transparent. The thermoplastic material of the first and second adjacent layers 20,20' may, preferably, be low-density polyethylene, medium-density polyethylene, polypropylene, polyester or polybutylene. The thermoplastic material of the first and second adjacent layers 20,20', most preferably, is low-density polyethylene. Those skilled in the art will recognize, however, that other flexible thermoplastic materials including biodegradable materials may be used as the thermoplastic material of the first and second adjacent layer 20,20'. The first and second adjacent layers 20,20' preferably have a thickness of from 0.00120 to 0.00130 mils and most preferably have a thickness of 0.00125 mils. The thermoplastic material of the first and second adjacent layers 20,20' aids in the retention and reflection of body heat and provides puncture resistance to the drape.

In this embodiment and as noted above, the outer layer 22 of flexible non-woven sterilizable material may be attached to either the first or second adjacent layer 20,20'. In a preferred embodiment, the outer layer 22 of flexible non-woven sterilizable material is not absorbent and non-permeable thereby maintaining sterility. In a most preferred embodiment, the outer layer 22 of flexible non-woven sterilizable material is a lightweight wet formed two-phase latex bonded non-woven fabric treated to impart water and alcohol repellency. The layer 22 of flexible non-woven sterilizable material may be one or a blend of cotton, polyester, rayon, polypropylene or cellulose. The material is preferably synthetic. Suitable materials are manufactured by The Dexter Corporation and Kimberly-Clark Corporation under the tradename K-cell. The layer 22 of flexible non-woven sterilizable material preferably has a thickness of from 0.0015 to 0.040 mils and most preferably has a thickness of 0.014 to 0.016 mils. The layer 22 of flexible non-woven sterilizable material is preferably attached to the first or second adjacent layer 20,20' using an adhesive. The adhesive is preferably moisture-proof and is most preferably an acrylic moisture-proof adhesive.

Additional embodiments of the invention are discussed below. The description of the materials comprising the above-discussed four-layer drape apply to these embodiments as well.

In a second embodiment of the present invention, the second adjacent layer 20' is omitted and the layer 22 of flexible non-woven sterilizable material is attached to the non-conductive core layer 18 of aluminum. The layer 22 of flexible non-woven sterilizable material is preferably attached to the non-conductive core layer 18 of aluminum using an adhesive. The adhesive is preferably moisture-proof and is most preferably an acrylic moisture-proof adhesive.

In a third embodiment of the present invention, the first adjacent layer 20 is omitted and the layer 22 of flexible non-woven sterilizable material is attached to the second adjacent layer 20'. The non-conductive core layer 18 of aluminum is vacuum deposited on the second adjacent layer 20'.

In a fourth embodiment of the present invention, the layer 22 of flexible non-woven sterilizable material is omitted. In this embodiment, the surgical drape of the present invention comprises the non-conductive core layer 18 of aluminum and the first and second adjacent layers 20,20'.

In a fifth embodiment of the present invention, the layer 22 of flexible non-woven sterilizable material and the second adjacent layer 20' are omitted. In this embodiment, the surgical drape of the present invention comprises the non-conductive core layer 18 of aluminum and the first adjacent layer 20.

In a sixth embodiment, the surgical drape of the present invention comprises a non-conductive first layer of aluminum and a second adjacent layer of flexible non-woven sterilizable material. The non-conductive first layer of aluminum is vacuum deposited on the second adjacent layer of flexible non-woven sterilizable material.

In a seventh embodiment, the surgical drape of the present invention comprises a non-conductive core layer of aluminum and first and second adjacent layers of flexible non-woven sterilizable material. The non-conductive core layer of aluminum is vacuum deposited on the first adjacent layer of flexible non-woven sterilizable material and the second adjacent layer of flexible non-woven sterilizable material is attached to the non-conductive first layer of aluminum using an adhesive.

The reflective surgical drape of the present invention was tested for conductivity. The tests conducted utilized both 60 cycle per second current (line power) and radio frequency current (electrosurgical power). Contact to the material was made with standard monitoring electrodes as well as by mechanically abrading the surface of the material. At 120 volts 60 cycles per second the resistance was determined to be in excess of 1 megaohm and well within the range of safety. At frequencies common to electrosurgery units it was determined that the material passed less than 1/10 the current (or 1/100 the power) that would pass through a patient at a maximum power of over 100 watts R.F. from an electrosurgical generator. This test simulated a worst case scenario of applying a cutting electrode directly to the reflective surgical drape. The inability of the reflective surgical drape of the present invention to conduct current is attributable to the non-continuous layer of aluminum that is vacuum deposited or sputtered on a thermoplastic or a non-woven layer. The aluminum layer would need to be continuous and many times thicker to perform as a conductor in a significant manner. These tests indicate that the reflective surgical drape of the present invention poses no problem when used in the presence of line voltage or electrosurgical generators.

The reflective surgical drape of the present invention provides many safety features, the most important of which are its nonconductivity and its resistance to puncture. The drape is also inert to alcohol and betadine which insures that the drape maintains its integrity throughout a surgical procedure.

While the present invention has been described in detail and with reference to specific examples thereof, it will be apparent to one skilled in the art that various changes and modifications can be made therein without departing from the spirit and scope thereof.

What is claimed is:

1. A sterilizable reflective surgical drape for covering at least a portion of and reducing heat loss from a surgical patient's body, comprising:
   (a) a non-conductive core layer of aluminum;
   (b) a first thermoplastic material layer superposed on said core layer;
   (c) a second thermoplastic material layer superposed on said core layer; and
   (d) a layer of flexible non-woven sterilizable material superposed on said first thermoplastic material layer.

2. A sterilizable reflective surgical drape according to claim 1 wherein said non-conductive core layer of aluminum is non-continuous.

3. A sterilizable reflective surgical drape according to claim 1, wherein said non-conductive core layer of aluminum is vacuum deposited to said first thermoplastic material layer.

4. A sterilizable reflective surgical drape according to claim 3, wherein said vacuum deposited non-conductive aluminum has a thickness of from 270 Å to 330 Å.

5. A sterilizable reflective surgical drape according to claim 4, wherein said vacuum deposited non-conductive aluminum has a thickness of 300 Å.

6. A sterilizable reflective surgical drape according to claim 3, wherein said second thermoplastic material layer is laminated with an adhesive to said non-conductive core layer of aluminum.

7. A sterilizable reflective surgical drape according to claim 6, wherein said adhesive is acrylic and moisture proof.

8. A sterilizable reflective surgical drape according to claim 1, wherein said thermoplastic material of said first and second thermoplastic material layers is selected from the group consisting of low-density polyethylene, medium-density polyethylene, polypropylene, polyester and polybutylene.

9. A sterilizable reflective surgical drape according to claim 8, wherein said thermoplastic material of said first and second thermoplastic material layers is low-density polyethylene.

10. A sterilizable reflective surgical drape according to claim 1, wherein said first and second thermoplastic material layers each have a thickness of from 0.00120 to 0.00130 mils.

11. A sterilizable reflective surgical drape according to claim 10, wherein said first and second thermoplastic material layers each have a thickness of 0.00125 mils.

12. A sterilizable reflective according to claim 2, wherein said layer of flexible non-woven sterilizable material is nonabsorbent and nonpermeable.

13. A sterilizable reflective surgical drape according to claim 1, wherein said layer of flexible non-woven sterilizable material comprises a lightweight wet formed two-phase latex bonded non-woven fabric treated to impart water and alcohol repellency.

14. A sterilizable reflective surgical drape according to claim 1, wherein said layer of flexible non-woven sterilizable material is one or a blend of cotton, polyester, rayon, polypropylene or cellulose.

15. A sterilizable reflective surgical drape according to claim 14, wherein said layer of flexible non-woven sterilizable material has a thickness of from 0.0015 to 0.040 mils.

16. A sterilizable reflective surgical drape according to claim 15, wherein said layer of flexible non-woven sterilizable material has a thickness of from 0.014 to 0.016 mils.

17. A sterilizable reflective surgical drape according to claim 14, wherein said layer of flexible non-woven sterilizable material is attached with an adhesive to said first thermoplastic material layer.

18. A sterilizable reflective surgical drape according to claim 17, wherein said adhesive is acrylic and moisture proof.

19. A sterilizable reflective surgical drape for covering at least a portion of and reducing heat loss from a surgical patient's body, comprising:
   (a) a non-conductive layer of aluminum;
   (b) a thermoplastic material layer superposed on said non-conductive layer of aluminum; and
   (c) a flexible non-woven sterilizable material layer superposed on said non-conductive layer of aluminum.

20. A sterilizable reflective surgical drape for covering at least a portion of and reducing heat loss from a surgical patient's body, comprising:
   (a) a non-conductive layer of aluminum;
   (b) a thermoplastic material layer superposed on said non-conductive layer of aluminum; and
   (c) a flexible non-woven sterilizable material layer superposed on said thermoplastic material layer.

21. A sterilizable reflective surgical drape for covering at least a portion of and reducing heat loss from a surgical patient's body, comprising:
   (a) anon-conductive layer of aluminum; and
   (b) a thermoplastic material layer superposed on said non-conductive layer of aluminum.

22. A sterilizable reflective surgical drape according to claim 21, further comprising:
   (c) an additional thermoplastic material layer superposed on said non-conductive layer of aluminum.

23. A sterilizable reflective surgical drape for covering at least a portion of and reducing heat loss from a surgical patient's body, comprising:
   (a) a non-conductive layer of aluminum; and
   (b) a flexible non-woven sterilizable material layer superposed on said non-conductive layer of aluminum.

24. A sterilizable reflective surgical drape according to claim 23, further comprising:
   (c) an additional flexible non-woven sterilizable material layer superposed on said non-conductive layer of aluminum.

25. A sterilizable reflective surgical drape for covering at least a portion of and reducing heat loss from a surgical patient's body, comprising:
   (a) a non-conductive metallized plastic sheeting; and
   (b) a thermoplastic material layer superposed on said metallized plastic sheeting.

26. A sterilizable reflective surgical drape according to claim 25, further comprising:
   (c) a flexible non-woven sterilizable material layer superposed on said thermoplastic material layer.

27. A sterilizable reflective surgical drape for covering at least a portion of and reducing heat loss from a surgical patient's body, comprising:
   (a) non-conductive metallized plastic sheeting; and
   (b) a flexible non-woven sterilizable material layer superposed on said metallized plastic sheeting.

* * * * *

UNITED STATES PATENT AND TRADEMARK OFFICE
CERTIFICATE OF CORRECTION

PATENT NO. : 4,945,924

DATED : August 7, 1990

INVENTOR(S) : Robert J. Poettgen

It is certified that error appears in the above-identified patent and that said Letters Patent is hereby corrected as shown below:

```
Column 1, line 16, change "Patients" to -- patients --.
Column 1, line 18, change "Part" to -- part --.
Column 1, line 22, change "Production" to -- production --.
Column 1, line 49, change " α " to a hyphen.
Column 3, line 8, change "Preven-" to -- preven- --.
Column 3, line 60, change "Poses" to -- poses --.
Column 4, line 24, change "resPect" to -- respect --.
Column 5, line 31, change "patient s" to -- patient's --.
Column 6, line 15, change "20" to -- 20' --.
```

In the Claims: Column 10,

Claim 21, line 4, change "anon-conductive" to -- a non-conductive --.

Signed and Sealed this

Nineteenth Day of November, 1991

*Attest:*

HARRY F. MANBECK, JR.

*Attesting Officer*  *Commissioner of Patents and Trademarks*